(12) United States Patent
Deniega et al.

(10) Patent No.: US 7,004,923 B2
(45) Date of Patent: Feb. 28, 2006

(54) CATHETER FOR UNIFORM DELIVERY OF MEDICATION

(75) Inventors: Jose Castillo Deniega, Lake Forest, CA (US); Roger Massengale, Mission Viejo, CA (US); Kenneth W. Rake, Laguna Niguel, CA (US)

(73) Assignee: I-Flow Corporation, Lake Forest, CA (US)

( * ) Notice: Subject to any disclaimer, the term of this patent is extended or adjusted under 35 U.S.C. 154(b) by 0 days.

(21) Appl. No.: 10/104,171

(22) Filed: Mar. 21, 2002

(65) Prior Publication Data

US 2003/0181887 A1 Sep. 25, 2003

Related U.S. Application Data

(63) Continuation of application No. 10/031,913, filed as application No. PCT/US00/19746 on Jul. 19, 2000, which is a continuation-in-part of application No. 09/363,228, filed on Jul. 19, 1999, now Pat. No. 6,350,253.

(51) Int. Cl.
*A61M 5/00* (2006.01)
*A61M 25/00* (2006.01)
*A61M 31/00* (2006.01)

(52) U.S. Cl. .......................... 604/4; 604/524; 604/264; 604/48

(58) Field of Classification Search .. 604/95.04–95.05, 604/220, 264, 523–525, 252, 8, 164.02, 282, 604/93.01, 27, 167–164, 4–48, 324–328; 600/585; 606/108
See application file for complete search history.

(56) References Cited

U.S. PATENT DOCUMENTS

| | | | |
|---|---|---|---|
| 3,595,241 A | | 7/1971 | Sheridan |
| 3,821,956 A | | 7/1974 | Gordhamer |
| 3,841,308 A | | 10/1974 | Tate |
| 3,938,529 A | * | 2/1976 | Gibbons ........................ 604/8 |
| 4,976,689 A | * | 12/1990 | Buchbinder et al. ..... 604/95.04 |

(Continued)

*Primary Examiner*—Nicholas D. Lucchesi
*Assistant Examiner*—Roz Maiorino
(74) *Attorney, Agent, or Firm*—Knobbe, Martens, Olson & Bear LLP

(57) ABSTRACT

The present invention provides a catheter for the delivery of fluid medication across an anatomical region. In accordance with one embodiment, the catheter comprises an elongated tube with a plurality of exit holes along an infusion section of the catheter, and an elongated flexible porous member residing within the tube and forming an annular space between the tube and the member. In accordance with other embodiments, the catheter includes a tube having a plurality of exit holes in a side wall of the tube. The exit holes may combine to form a flow-restricting orifice of the catheter. Advantageously, fluid within the catheter flows through all of the exit holes, resulting in uniform distribution of fluid within an anatomical region. In one particular embodiment, the catheter comprises a tube having elongated exit slots therein. In accordance with other embodiments, the catheter includes an elongated tubular member made of a porous membrane. The porous membrane is configured so that a fluid introduced into an open end of the tubular member will flow through side walls of the tubular member at a substantially uniform rate along a length of the tubular member. In accordance with other embodiments, the catheter includes an elongated "weeping" tubular coil spring attached to an end of, or enclosed within, a tube. Fluid within the spring and greater than or equal to a threshold pressure advantageously flows radially outward between the spring coils. Advantageously, the fluid is dispensed substantially uniformly throughout a length of the spring.

30 Claims, 5 Drawing Sheets

U.S. PATENT DOCUMENTS

| | | |
|---|---|---|
| 5,066,278 A | 11/1991 | Hirschberg et al. |
| 5,184,627 A | 2/1993 | de Toledo |
| 5,201,723 A * | 4/1993 | Quinn .................. 604/264 |
| 5,267,979 A | 12/1993 | Appling et al. |
| 5,269,755 A | 12/1993 | Bodicky |
| 5,356,388 A | 10/1994 | Sepetka et al. |
| 5,376,083 A | 12/1994 | Mische |
| 5,405,316 A * | 4/1995 | Magram .................. 604/8 |
| 5,425,723 A | 6/1995 | Wang |
| 5,569,219 A * | 10/1996 | Hakki et al. ............. 604/524 |
| 5,643,228 A | 7/1997 | Schucart et al. |
| 5,702,372 A | 12/1997 | Nelson |
| 5,709,874 A | 1/1998 | Hanson et al. |
| 5,776,111 A | 7/1998 | Tesio |
| 5,800,407 A | 9/1998 | Eldor |
| 5,833,652 A | 11/1998 | Preissman et al. |
| 5,846,216 A | 12/1998 | Gonzales et al. |
| 6,123,688 A * | 9/2000 | Botich et al. ............. 604/220 |
| 6,350,253 B1 * | 2/2002 | Deniega et al. ......... 604/164.02 |
| 6,623,449 B1 * | 9/2003 | Paskar .................. 604/95.04 |
| 6,676,643 B1 * | 1/2004 | Brushey ................. 604/264 |
| 2002/0082547 A1 * | 6/2002 | Deniega et al. |
| 2002/0133142 A1 * | 9/2002 | Deiega et al. |
| 2003/0158538 A1 * | 8/2003 | Deniega et al. ........... 604/523 |
| 2004/0064129 A1 * | 4/2004 | Deniega et al. ........... 604/523 |

* cited by examiner

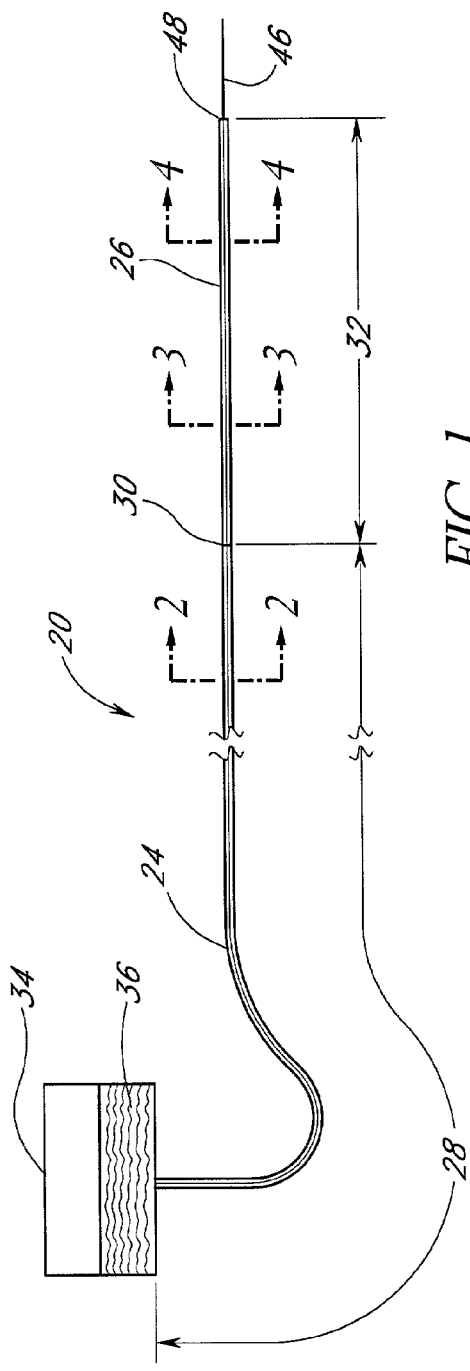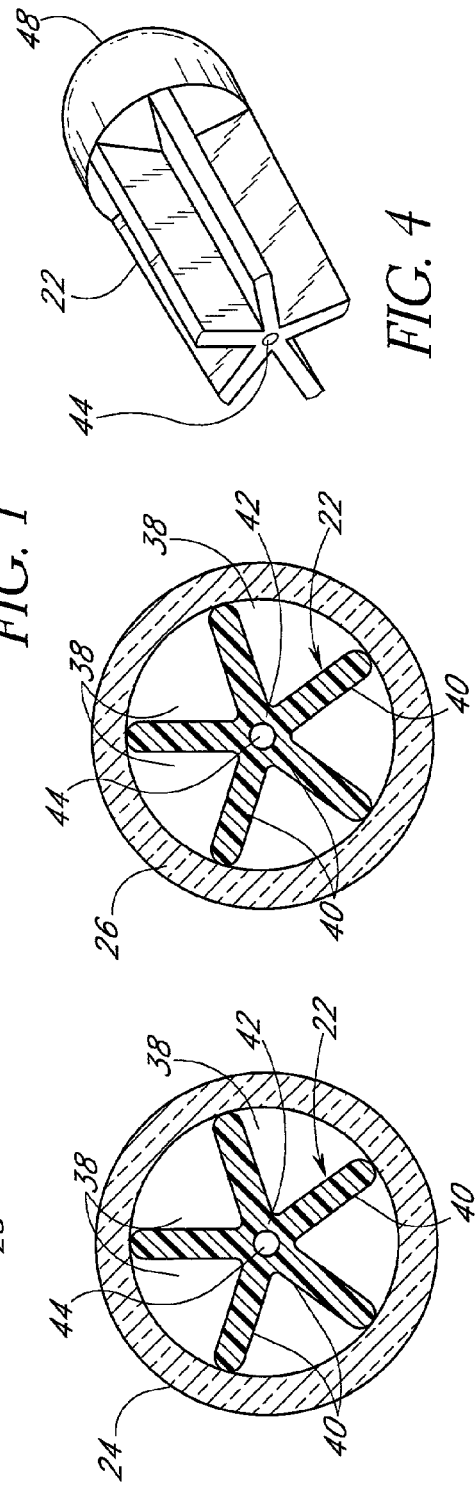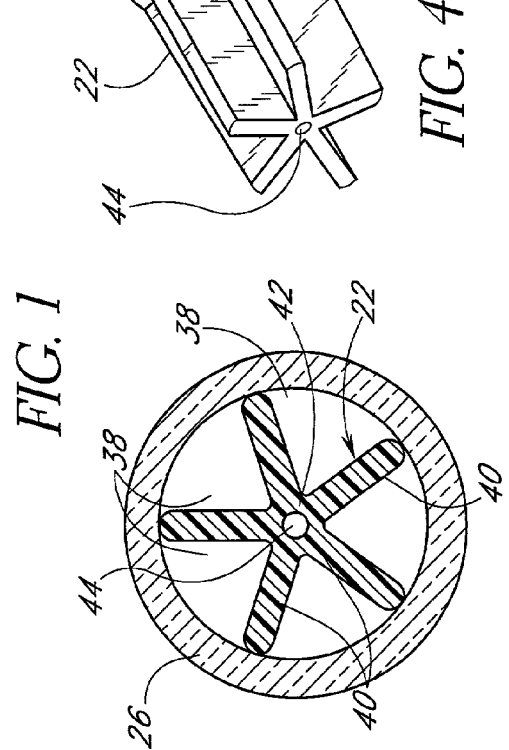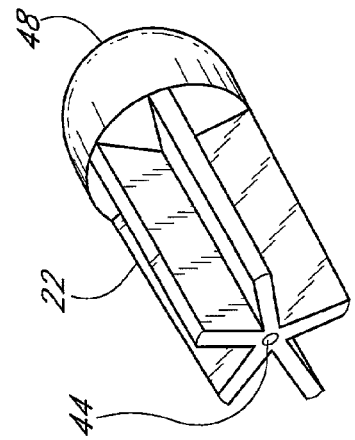

CATHETER FOR UNIFORM DELIVERY OF MEDICATION

PRIORITY INFORMATION

This application is a continuation of copending U.S. patent application Ser. No. 10/031,913, filed May 21, 2002; which is the National Stage of International Application No. PCT/US00/19746, filed Jul. 19, 2000 and published in English; which is a continuation-in-part of U.S. patent application Ser. No. 09/363,228, filed Jul. 19, 1999, now U.S. Pat. No. 6,350,253, the entireties of which are expressly incorporated by reference.

BACKGROUND OF THE INVENTION

1. Field of the Invention

This invention generally relates to catheters and, in particular, to a catheter that delivers fluid medication uniformly across an infusion section of the catheter.

2. Description of the Related Art

Infusion catheters for delivery of fluid medication into anatomical systems, such as the human body, are well known in the art. Such catheters generally include a flexible hollow tube inserted into some region of the anatomy. The tube typically contains one or more axial lumens within which the fluid may flow. The proximal end of the catheter tube is connected to a fluid source from which fluid is introduced into the catheter tube. The fluid flows within one of the lumens under pressure supplied at the proximal end of the tube. For each lumen, there are commonly provided one or more exit holes along an infusion section near the distal end of the tube, for fluid to exit the tube. Such exit holes are created by piercing the side wall of the hollow tube.

In certain medical conditions, it is advantageous to deliver fluid medication to a plurality of sites within a wound area. For instance, some wounds which require pain medication may be in communication with many nerve endings, rather than a single nerve trunk. One example of such a wound is a surgical incision. As stated above, it is known to provide a plurality of exit holes through which the fluid medication exits the catheter tube. The exit holes may be provided at various axial and circumferential positions along the catheter tube in order to control the position of the medication delivery sites. An example of a catheter having this configuration is disclosed in U.S. Pat. No. 5,800,407 to Eldor. Also, in some cases it is desirable to deliver such medication under low pressure, so that the fluid is delivered at a relatively low rate. For example, some pain medications must be delivered slowly to avoid toxicity and other side effects. Furthermore, in many cases it is desirable to dispense fluid medication at a substantially uniform rate throughout the infusion section of the catheter, so that the medication is evenly distributed throughout the wound area.

Unfortunately, a limitation of prior art catheters with multiple exit holes, such as the catheter taught by Eldor, is that during low pressure delivery of fluid medication the fluid tends to exit only through the exit hole(s) nearest to the proximal end of the infusion section of the catheter tube. This is because fluids flowing through a tube more readily exit through the exit holes offering the least flow resistance. The longer the flow path followed by the fluid in the lumen, the higher the flow resistance and pressure drop experienced by the fluid. The most proximal holes offer the least flow resistance and pressure drop. Therefore, the fluid tends to exit the catheter tube primarily through these exit holes. As a result, the fluid medication is delivered only to a small region within the wound area. The tendency of the fluid to undesirably flow only through the most proximal exit holes depends upon the hole size, the total number of exit holes, and the flow rate. As the hole size or number of holes increases, the fluid becomes more likely to exit only through the most proximal holes. Conversely, as the flow rate increases, the fluid becomes less likely to do so.

The tendency of the fluid to undesirably exit only through the most proximal holes of the catheter can in some cases be overcome by increasing the flow rate or pressure of the fluid, which causes the fluid to flow through more of the exit holes of the catheter. Indeed, if the flow rate or pressure is sufficiently high, the fluid will flow through all of the exit holes. However, sometimes it is medically desirable to deliver medication at a relatively slow rate, i.e., at a low pressure. Also, even in those cases in which high pressure fluid delivery is acceptable or desirable, prior art catheters do not provide for uniform fluid delivery along the infusion section of the catheter. Rather, the flow rate through the exit holes nearer to the proximal end of the infusion section tends to be greater than that through the exit holes nearer to the distal end. This is because the fluid passing through the more proximal holes experiences a lower flow resistance and pressure drop. In contrast, the fluid flowing through the more distal holes experiences greater flow resistance and pressure drop, and consequently exits at a lower flow rate. The further distal the hole, the lower the exit flow rate of the fluid. As a result, there is an uneven distribution of medication throughout the wound area.

In another known type of infusion catheter, several lumens are provided within a catheter tube. For each lumen, one exit hole is provided by piercing a hole within the wall of the tube. The exit holes are provided at different axial positions along the infusion section of the catheter tube. In this manner, fluid medication may be delivered to several positions within the wound area. While this configuration offers improved fluid distribution, it has some disadvantages. One disadvantage is that the fluid flow rates through the exit holes are not equal, since the more distal exit holes offer a greater flow resistance for the same reasons discussed above. Another disadvantage is that the number of lumens, and consequently the number of fluid exit holes, is limited by the small diameter of the catheter tube. As a result, fluid may be delivered only to a very limited number of positions within the wound area. Yet another disadvantage is that the proximal ends of the lumens must be attached to a complicated manifold which increases the cost of manufacturing the catheter.

An example of a catheter providing a more uniform dispensation of fluid medication throughout an infusion section of the catheter is illustrated by U.S. Pat. No. 5,425,723 to Wang. Wang discloses an infusion catheter including an outer tube, an inner tube concentrically enclosed within the outer tube, and a central lumen within the inner tube. The inner tube has a smaller diameter than the outer tube, so that an annular passageway is formed therebetween. The outer tube has a plurality of evenly spaced exit holes defining the infusion section of the catheter. In use, fluid flowing within the central lumen passes through strategically positioned side holes within the side walls of the inner tube. In particular, the spacing between adjacent side holes decreases along a length of the inner tube to induce more fluid to pass through the more distal side holes. The fluid then flows longitudinally through the annular passageway before exiting through the exit holes in the outer tube wall. In the annular passageway, the fluid can flow in a distal or proximal direction, depending on the location of the nearest exit hole in the outer tube. This configuration is provided to induce a more uniform exit flow rate of fluid from the catheter.

Unfortunately, the Wang catheter is only effective for relatively high pressure fluid delivery. When used for relatively low pressure fluid delivery, the catheter disclosed by Wang does not provide uniform dispensation of fluid. Instead, the fluid tends to exit through the side holes of the inner and outer tubes that are nearest to the proximal end of the infusion section of the catheter, since these holes offer the least flow resistance. Even for high pressure fluid delivery, there are several limitations of this design. One limitation is that the concentric tubes design is relatively complex and difficult to manufacture. Both tubes must be flexible enough to permit maneuverability through an anatomical system, yet the annular passageway must remain open so that fluid may flow uniformly therein. Another limitation is that the annular passageway may be disturbed if there is a bend in the infusion section of the tube. A bend in the catheter may deform the annular passageway or even cause the inner and outer tubes to come into contact. This can cause an uneven fluid pressure within a longitudinal cross-section of the annular passageway, resulting in non-uniform fluid delivery.

Thus, there is a need for an improved infusion catheter for delivering fluid medication uniformly along its infusion section in a relatively simple, easy to manufacture design which is effective for both high flow rate and low flow rate fluid delivery. Furthermore, it is recognized that a particular class of catheters, such as the Wang catheter, may provide uniform fluid delivery only at high fluid pressure or flow rates. However, there is a need for an infusion catheter belonging to this class that has a relatively simple, easy to manufacture design and can maintain uniform fluid delivery while bent or otherwise physically deformed.

SUMMARY OF THE INVENTION

Accordingly, it is a principle object and advantage of the present invention to overcome some or all of these limitations and to provide an improved catheter for delivering fluid medication to a wound area of an anatomical region.

In accordance with one embodiment the present invention a catheter is provided for the uniform delivery of fluid across an anatomical region, comprising an elongated tubular member made of a porous membrane. The membrane is sized to be inserted through a subcutaneous layer surrounding the anatomical region, such as a person's skin. The membrane is configured so that a fluid introduced under pressure into an open end of the tubular member will flow through side walls of the tubular member at a substantially uniform rate along a length of the tubular member. The present invention also provides a method of uniformly delivering fluid throughout an anatomical region, comprising the steps of inserting the elongated tubular member into the anatomical region and introducing a fluid under pressure into an open end of the tubular member.

Another embodiment of the present invention provides a catheter and method for the uniform delivery of fluid throughout an anatomical region. The catheter comprises an elongated support and a porous membrane wrapped around the support. The support is configured so that one or more lumens are formed between the support and the membrane. Alternatively, the support may be a tubular member having a plurality of holes therein. The method comprises the steps of inserting the above-described catheter into the anatomical region and introducing a fluid under pressure into the proximal end of at least one of the lumens. Advantageously, the fluid passes through the membrane at a substantially uniform rate into the anatomical region. The present invention further provides a method of manufacturing this catheter comprising the steps of forming an elongated support and wrapping a porous membrane around the support so that one or more lumens are formed between the support and the membrane.

Another embodiment of the present invention provides a catheter and method for the uniform delivery of fluid throughout an anatomical region. The catheter comprises an elongated tube including a plurality of exit holes along a length thereof and a tubular porous membrane concentrically enclosed within the tube. The tube and membrane define a lumen. The method comprises the steps of inserting the above-mentioned catheter into the anatomical region and introducing a fluid under pressure into the proximal end of the lumen so that the fluid advantageously passes through the membrane and the exit holes at a substantially uniform rate into the anatomical region. The present invention further provides a method of manufacturing this catheter, comprising the steps of forming an elongated tube, providing a plurality of exit holes along a length of the tube, forming a tubular porous membrane, and concentrically enclosing the tubular porous membrane within the tube so that the tube and membrane define a lumen.

Yet another embodiment of the present invention provides a device and method for the uniform delivery of fluid throughout an anatomical region. The device is advantageously simple and easy to manufacture, comprising an elongated catheter having a plurality of exit holes along a length thereof. The exit holes may serve as the flow-restricting orifice. Alternatively, a flow-restricting orifice may be provided elsewhere within the catheter or proximal to the catheter. The exit holes may gradually increase in size along the length of the catheter, so that the largest exit hole is further distal than the smallest exit hole. Alternatively, the holes can be laser drilled and be of approximately the same size. Advantageously, a fluid flowing under pressure within the catheter will flow through substantially all of the exit holes at a substantially equal rate. The method comprises the steps of inserting the catheter into the anatomical region and introducing a fluid under pressure into the proximal end of the catheter. The fluid flows through the exit holes and enters the anatomical region, advantageously flowing through substantially all of the exit holes at a substantially equal rate. The present invention further provides a method of manufacturing this device, comprising the steps of forming an elongated catheter and providing a plurality of exit holes along a length of the catheter in a manner so that the exit holes gradually increase in size along the length of the catheter from the proximal end to the distal end thereof.

Yet another embodiment of the present invention provides a catheter and method for delivering fluid medication to an anatomical region. The catheter comprises a tube, a "weeping" tubular coil spring attached to a distal end of the tube, and a stop closing a distal end of the spring. The tube and spring each define a portion of a central lumen. The spring has adjacent coils in contact with one another so that fluid within the spring and below a threshold dispensation pressure is prevented from exiting the lumen by flowing radially between the coils. The spring has the property of stretching when the fluid pressure is greater than or equal to the threshold dispensation pressure permitting the fluid to be dispensed from the lumen by flowing radially between the coils, i.e. "weeping" through the spring. Alternatively, the fluid may weep through imperfections in the spring coil.

Advantageously, the fluid is dispensed substantially uniformly throughout the length and circumference of a portion of the spring. In use, fluid is introduced into an open proximal end of the tube, allowed to flow into the spring, and brought to a pressure greater than or equal to the threshold dispensation pressure so that the fluid weeps through the spring.

Yet another embodiment of the present invention provides a catheter and method for delivering fluid medication to an anatomical region. The catheter comprises a distally closed tube and a "weeping" tubular coil spring, as described above, concentrically enclosed within the tube. A plurality of exit holes are provided in side walls along a length of the tube, defining an infusion section of the tube. The spring is enclosed within the infusion section so that a lumen is defined within the tube and spring. In use, fluid is introduced into a proximal end of the tube, allowed to flow into the spring, and brought to a pressure greater than or equal to the threshold dispensation pressure of the spring so that the fluid is dispensed from the lumen by weeping through the spring and then flowing through the exit holes of the tube.

Yet another embodiment of the present invention provides a catheter comprising an elongated tube and a solid flexible member positioned within the tube. The tube has a closed distal end and a plurality of exit holes in side walls of the tube. The exit holes are provided along a length of the tube defining an infusion section of the catheter. The tube is sized to be inserted into an anatomical region. The member is positioned within the tube and is sized so that an annular space is formed between the tube and the member. The member is formed of a porous material. Advantageously, the catheter is configured so that a fluid introduced into a proximal end of the tube will flow through the exit holes at a substantially uniform rate throughout the infusion section.

In yet another embodiment, the present invention provides a catheter comprising an elongated tube having a plurality of exit slots in side walls of the tube. The slots are provided along a length of the tube defining an infusion section of the catheter. The exit slots are oriented generally parallel to the longitudinal axis of the tube. Advantageously, the tube is configured so that a fluid flowing therein will flow through substantially all of the exit slots at a substantially equal rate. In one optional aspect, the slots increase in length from the proximal to the distal ends of the infusion section.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 1 is a schematic side view of a catheter having features and advantages in accordance with a first embodiment of the present invention;

FIG. 2 is a sectional view of the catheter of FIG. 1, taken along line 2—2 of FIG. 1;

FIG. 3 is a sectional view of the catheter of FIG. 1, taken along line 3—3 of FIG. 1;

FIG. 4 is a perspective view of the end portion and support beam of the catheter of FIG. 1, illustrating a cross-section taken along line 4—4 of FIG. 1;

DETAILED DESCRIPTION OF THE PREFERRED EMBODIMENTS

Figure 8:
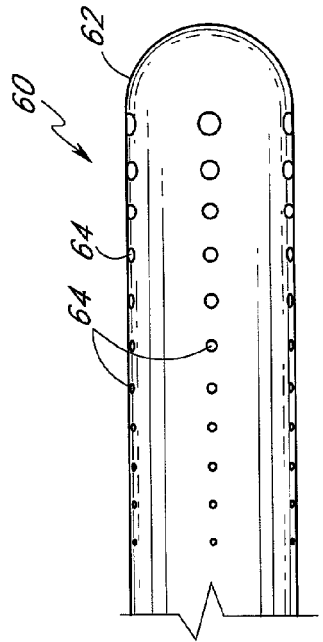
FIG. 8 is a side view of a catheter having features and advantages in accordance with a fourth embodiment of the present invention.

FIGS. 1–4 illustrate an infusion catheter 20 according to one embodiment of the present invention. Catheter 20 preferably includes a flexible support 22 (FIGS. 2–4), a non-porous membrane 24, and a porous membrane 26. The membranes 24 and 26 are wrapped around the support 22 to form a plurality of axial lumens between the inner surfaces of the membranes 24 and 26 and the surface of the support 22, as described in greater detail below. The non-porous membrane 24 defines a non-infusing section 28 of the catheter 20, and preferably covers the support 22 from the proximal end thereof to a point 30, shown in FIG. 1. Similarly, the porous membrane 26 defines an infusion section 32 of catheter 20, and preferably covers the support 22 from the point 30 to the distal end of support 22. Alternatively, the catheter 20 may be configured without a non-porous membrane 24. In this configuration, the porous membrane 26 covers the entire length of the support 22, so that the entire length of the support 22 corresponds to the infusion section of the catheter 20. The infusion section can have any desired length. The proximal end of the catheter 20 may be connected to a fluid supply 34 containing a fluid 36 such as a liquid medication. The distal end of catheter 20 may include a cap 48 (FIG. 4) defining the endpoint of the axial lumens within the catheter 20.

In use, the catheter 20 is inserted into an anatomical system, such as a human body, to deliver fluid medication directly to a wound area within the anatomical system. In particular, the catheter 20 is designed to deliver medication throughout a generally linear segment of the wound area, corresponding to the infusion section 32 of the catheter 20. Thus, the catheter is preferably inserted so that the infusion section 32 is positioned within the wound area. By using well known methods, a physician or nurse may insert the catheter 20 with the aid of an axial guide wire 46 positioned within an axial guide wire lumen 44 of the catheter. Once the catheter is positioned as desired, the guide wire 46 is simply pulled back out through the proximal end of the catheter 20. Alternatively, the catheter 20 may be provided without a guide wire or a guide wire lumen.

FIGS. 2 and 3 illustrate a preferred configuration of the support 22. The surface of the support 22 includes interruptions such as a plurality of ribs 40 as shown in the figures. The interruptions are configured so that when the membranes 24 and 26 are wrapped around the support 22, the membranes form a portion of the walls of a plurality of axial lumens 38 within which the fluid 36 may flow. In a preferred configuration, a plurality of ribs 40 extend radially from a common axial center portion 42 of the support 22. The ribs 40 also extend longitudinally along a length of the support 22, and preferably along the entire length thereof. In the non-infusing section 28, shown in FIG. 2, the non-porous membrane 24 is preferably tightly wrapped around the outer edges of the ribs 40. As a result, the axial lumens 38 are formed between the inner surface of the non-porous membrane 24 and the outer surface of support 22. Similarly, in the infusion section 32, shown in FIG. 3, the porous membrane 26 is preferably tightly wrapped around the outer edges of the ribs 40, so that the axial lumens 38 are formed between the inner surface of porous membrane 26 and the outer surface of support 22.

In an alternative embodiment of the catheter 20, the porous membrane 26 may be wrapped around the entire length of the support 20, thus replacing the non-porous membrane 24. In this embodiment, the entire length of the support 22 corresponds to the infusion section 32. According to another alternative embodiment, the support 22 may extend only within the infusion section 32, and a tube may be provided extending from the fluid supply 34 to the proximal end of the support 22. In this embodiment, the tube replaces the non-porous membrane 24 and the portion of the support 22 extending within the non-infusing section 28 of the preferred embodiment. In other words, the tube defines the non-infusing section 28.

In the preferred configuration, the number of ribs 40 equals the number of axial lumens 38. Although five ribs 40 and axial lumens 38 are shown in FIGS. 2 and 3, any suitable number of ribs 40 and lumens 38 may be provided, giving due consideration to the goals of providing a plurality of lumens within the catheter 20, maintaining flexibility, and, if desired, maintaining the fluid independence of the lumens. Herein, the terms "fluid independence," "fluid separation," and the like, when used to describe a plurality of axial lumens, simply mean that the lumens do not fluidly communicate with each other. The membranes 24 and 26 are preferably glued along the outer edges of the ribs 40, utilizing any suitable glue, such as a medical grade glue or epoxy. This prevents the membranes 24 and 26 from slipping, which might occur as the catheter is inserted or removed from the anatomy. More preferably, the membranes are glued along the entire length of the outer edges of each of the ribs 40. Alternatively, the membrane may be wrapped around the support and not secured to the support by a foreign substance. The membrane and support may also be secured to each other by other means known to those of skill in the art. This maintains the fluid independence of the lumens 38. If desired, an axial guide wire lumen 44 may be provided within the axial central portion 42 of the support 22. The guide wire lumen 44 is adapted to receive a guide wire 46 which may be used to aid in the insertion of the catheter 20 into the anatomy, as described above and as will be easily understood by those of skill in the art.

As shown in FIG. 4, the catheter 20 preferably includes an end portion or cap 48 secured to the distal end of support 22. End portion 48 may be formed integrally with the support 22 or may be adhesively bonded thereto. Preferably, the proximal end of end portion 48 is circular and has a diameter such that the outer surface of the proximal end of end portion 48 is aligned with the outer edges of the ribs 40 of the support 22, as shown. The porous membrane 26 is wrapped around the proximal end of the end portion 48. The membrane 26 is preferably glued to the end portion 48 so that fluid 36 within the lumens 38 is prevented from exiting the catheter 20 without passing through the walls of the membrane 26. End portion 48 blocks axial fluid flow through the distal end of catheter 20. However, end portion 48 may optionally be formed from a porous material to permit some axial dispensation of fluid from the distal end of the catheter 20, if desired. The distal end of end portion 48 is preferably dome-shaped, as shown, to permit the catheter 20 to more easily be inserted into an anatomical region.

The support 22 can be formed from a variety of materials, giving due consideration to the goals of flexibility, lightweight, strength, smoothness, and non-reactivity to anatomical systems, i.e., safety. Suitable materials for the support 22 include nylon, polyamide, teflon, and other materials known to those skilled in the art. The porous membrane 26 is preferably a sponge-like or foam-like material or a hollow fiber. The membrane 26 may be formed from a variety of suitable materials, giving due consideration to the goals of being flexible and non-reactive to anatomical systems. The membrane 26 preferably has a porosity resulting in substantially uniform dispensation of fluid along the surface area of the infusion section 32 of the catheter 20, and has an average pore size sufficiently small to limit the flow of bacteria through the membrane walls. Some suitable materials for the membrane 26 are polyethylene, polysulfone, polyethersulfone, polypropylene, polyvinylidene difluoride, polycarbonate, nylon, or high density polyethylene. These materials are advantageously biocompatible. The porous membrane 26 may filter out unwanted bacteria from the fluid medication as it passes through the membrane 26. It is known that the smallest bacteria cannot pass through a pore any smaller than 0.23 microns. Thus, the average pore size, or pore diameter, of the porous membrane 26 may be less than 0.23 microns to prevent bacteria from traversing the membrane 26. The average pore size, or pore diameter, of the membrane 26 is preferably within the range of about 0.1 to 1.2 microns, more preferably within the range of about 0.3 to 1 micron, and even more preferably about 0.8 microns.

As mentioned above, the proximal end of catheter 20 may be connected to a fluid supply 34. The catheter 20 may be configured so that each axial lumen 38 is fluidly independent. In other words, the lumens 38 would not fluidly communicate with one another. The catheter 20 may be connected to a single fluid supply 34, so that the fluid 36 flows within each of the lumens 38. Alternatively, the catheter 20 may be connected to a plurality of separate fluid supplies so that several different fluids may separately flow within the lumens 38. According to this configuration, each lumen 38 may be connected to a separate fluid supply so that the total number of different fluids that may be delivered to the anatomy is equal to the number of lumens 38. Alternatively, the fluid lumens need not be fluidly independent. For example, the membrane 26 may not be secured to the support 22 along the entire length of the support 22, thus permitting fluid 36 to migrate between lumens 38.

In operation, the catheter 20 delivers fluid directly to the area of the anatomy that is adjacent to the infusion section 32. The fluid 36 from the fluid source 34 is introduced into the axial lumens 38 at the proximal end of the catheter 20. The fluid 36 initially flows through the non-infusing section 28. When the fluid 36 first reaches the infusion section 32, it soaks into the porous membrane 26. As more fluid 36 enters the infusion section 32, it diffuses longitudinally within the walls of the membrane 26 until the entire membrane 26 and infusion section 32 are saturated with fluid. At this point the fluid 36 begins to pass through the membrane 26, thereby exiting the catheter 20 and entering the anatomy. Moreover, the fluid 36 advantageously passes through the entire surface area of the porous membrane 26 at a substantially uniform rate, due to the characteristics of the membrane 26. Thus, the fluid is delivered at a substantially equal rate throughout a generally linear segment of the wound area of the anatomy. Furthermore, this advantage is obtained for both low and high pressure fluid delivery.

Figure 5:
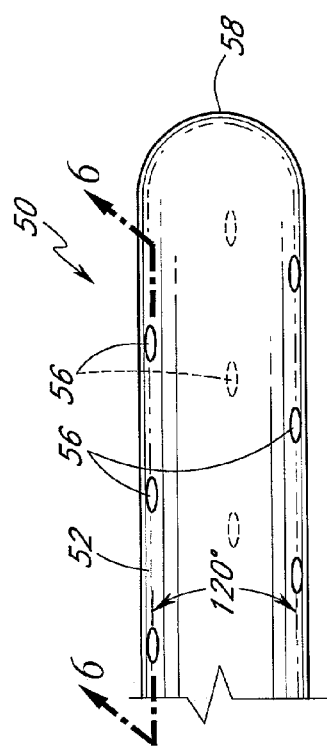
FIG. 5 is a side view of a catheter having features and advantages in accordance with a second embodiment of the present invention.
Figure 6:
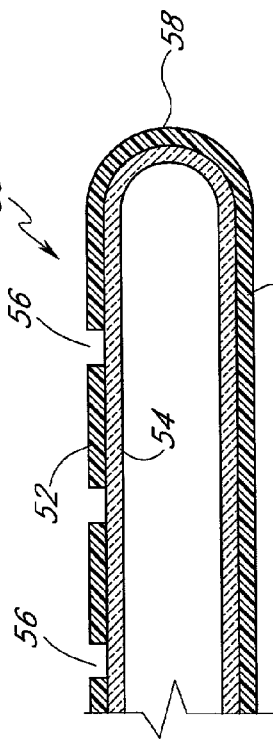
FIG. 6 is a cross-sectional view of the infusion section of the catheter of FIG. 5 taken along line 6—6 of FIG. 5.

FIGS. 5 and 6 illustrate a catheter 50 according to an alternative embodiment of the present invention. According to this embodiment, the catheter 50 includes an elongated outer tube 52 and an inner elongated tubular porous membrane 54. The tubular membrane 54 is preferably concentrically enclosed within the outer tube 52. More preferably, the tube 52 tightly surrounds and supports the tubular membrane 54 so that a relatively tight fit is achieved between the inner dimensions of tube 52 and the outer dimensions of membrane 54. A plurality of fluid exit holes 56 are provided within the tube 52, preferably throughout the entire circumference thereof. The portion of tube 52 that includes the exit holes 56 defines the infusion section of catheter 50. The tubular membrane 54 need only be provided along the length of the infusion section, but could be longer. Optionally, axial exit holes may be provided within the distal tip 58 of the tube 52. Also, a guide wire and/or guide wire lumen may be provided to aid in the insertion of the catheter 50 into the anatomy, as will be understood by those skilled in the art.

The tube 52 may be formed from any of a variety of suitable materials, such as nylon, polyimide, teflon and other materials known to those skilled in the art, giving due consideration to the goals of non-reactivity to anatomical systems, flexibility, light-weight, strength, smoothness, and safety. In a preferred configuration, the tube 52 is preferably a 20 gauge catheter tube, having inside and outside diameters of 0.019 inches and 0.031 inches, respectively. The exit holes 56 of tube 52 are preferably about 0.015 inches in diameter and provided at equally spaced axial positions along the tube 52. The holes 56 are preferably arranged so that every hole is angularly displaced about 120° relative to the longitudinal axis of the tube 52, from the angular location of the previous hole. The axial separation between adjacent exit holes 56 is preferably within the range of about 0.125 to 0.25 inches, and more preferably about 3/16 inch. Also, the infusion section can have any desirable length. This configuration results in a thorough, uniform delivery of fluid throughout a generally linear segment of the wound area. Of course, the exit holes 56 may be provided in any of a variety of alternative arrangements.

The tubular porous membrane 54 is preferably a sponge-like or foam-like material or a hollow fiber. The tubular membrane 54 may have an average pore size, or pore diameter, less than 0.23 microns to filter bacteria. The pore diameter is preferably within the range of about 0.1 to 1.2 microns, more preferably within the range of about 0.3 to 1 micron, and even more preferably about 0.8 microns. The tubular membrane 54 may be formed from any of a variety of suitable materials, giving due consideration to the goals of non-reactivity to anatomical systems, maintaining flexibility, fitting within the size constraints of the tube 52, and having a porosity resulting in the substantially uniform dispensation of fluid through all of the exit holes 56 in tube 52. Some suitable materials for the membrane 54 are polyethylene, polysulfone, polyethersulfone, polypropylene, polyvinylidene difluoride, polycarbonate, nylon, or high density polyethylene. Preferable inside and outside diameters of the tubular membrane 54 are 0.010 inches and 0.018 inches, respectively. In the event that a guide wire 46 is provided, the guide wire may be a stainless steel wire about 0.005 inches in diameter. The tube 52 may be secured to the membrane 54 by epoxy or other means known to those skilled in the art. Alternatively, the membrane 54 may contact the tube 52 with an interference fit and not use other materials to secure the membrane 54 in the tube 52.

In operation, the catheter 50 delivers fluid to the region of an anatomical system adjacent to the infusion section of catheter 50. As the fluid flows into the infusion section, it initially soaks into the tubular porous membrane 54. As more fluid enters the infusion section, the fluid diffuses longitudinally within the walls of the tubular member 54. Once the membrane 54 and the tubular space therein are saturated, the fluid passes through the membrane 54 and exits the catheter 50 by flowing through the exit holes 56 of the tube 52. Moreover, the fluid advantageously passes through the membrane substantially uniformly throughout the surface area of the membrane 54, resulting in a substantially uniform flow through substantially all of the exit holes 56. Thus, the fluid is delivered at a substantially equal rate throughout the wound area of the anatomy. Furthermore, this advantage is obtained for both low and high pressure fluid delivery.

Figure 7:
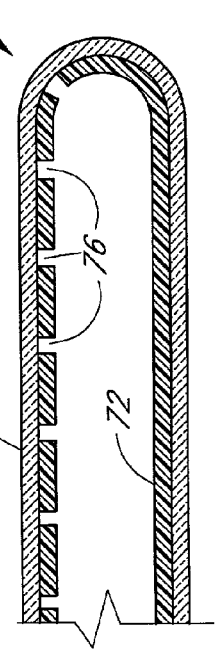
FIG. 7 is a cross-sectional view of a catheter having features and advantages in accordance with a third embodiment of the present invention.

FIG. 7 illustrates a catheter 70 according to another embodiment of the present invention. Catheter 70 includes a tube 72 having a plurality of exit holes 76 in side walls of the tube, and a tubular porous membrane 74 concentrically enclosing the tube 72. Catheter 70 operates in a similar manner to catheter 50 described above in connection with FIGS. 5 and 6. In use, fluid medication passes through the exit holes 76 and then begins to soak into the porous membrane 74. The fluid diffuses longitudinally within the walls of the membrane until the membrane is saturated. Thereafter, the fluid leaves the membrane walls and enters the anatomy. Advantageously, the fluid is dispensed to the anatomy at a substantially uniform rate throughout the surface area of the membrane 74. As in the previous embodiments, this advantage is obtained for both low and high pressure fluid delivery.

FIG. 8 illustrates a catheter 60 according to another embodiment of the present invention. Catheter 60 is better suited for relatively high flow rate delivery of fluid to a region within an anatomical system. Catheter 60 includes a tube 62 having a plurality of exit holes 64 of increasing size. In particular, the more distal exit holes are larger in diameter than the more proximal exit holes. The position of the exit holes 64 on the tube 62 defines the length of the infusion section of the catheter 60. The infusion section can have any desired length. The proximal end of catheter 60 is connected to a fluid supply, and a guide wire and/or guide wire lumen may also be provided for aiding in the insertion of catheter 60 into the anatomy.

As discussed above, for high or low pressure fluid delivery, exit holes nearer to the distal end of a catheter tube generally have increased flow resistance compared to exit holes nearer to the proximal end of the tube. Also, the fluid flowing through the more distal holes experiences a greater pressure drop. Consequently, there is generally a greater flow rate of fluid through the more proximal holes, resulting in non-uniform fluid delivery. In contrast, catheter 60 advantageously provides substantially uniform fluid delivery through substantially all of the exit holes 64, under relatively high flow rate conditions. This is because the larger size of the more distal holes compensates for their increased flow resistance and pressure drop. In other words, since the more distal holes are larger than the more proximal holes, there is a greater flow rate through the more distal holes than there would be if they were the same size as the more proximal holes. Advantageously, the holes 64 are provided in a gradually increasing size which results in substantially uniform fluid delivery. In addition, the exit holes 64 may be sized so that they combine to form a flow-restricting orifice, as described below in connection with the embodiment of FIG. 12.

As compared to prior art catheters, catheter 60 is advantageously simple and easy to manufacture. All that is required is to drill a plurality of exit holes 64 in the tube 62. Furthermore, catheter 60 can sustain greater bending than prior art catheters while maintaining operability. In contrast to prior art catheters, such as the Wang catheter, if the tube 62 is bent somewhat, it will still deliver fluid relatively uniformly. This is because the tube 62 has a single lumen with a relatively large cross-section. When the tube 62 is somewhat bent, fluid flowing within the lumen is less likely to experience blockage and a consequent pressure change which might lead to non-uniform fluid dispensation.

The tube 62 of catheter 60 may be formed from any of a wide variety of materials, giving due consideration to the goals of non-reactivity to anatomical systems, flexibility, light-weight, strength, smoothness, and safety. Suitable materials include nylon, polyimide, teflon, and other materials known to those skilled in the art. The infusion section can have any desired length but is preferably about 0.5 to 20 inches long, and more preferably about 10 inches long. The diameter of the exit holes 64 preferably ranges from about 0.0002 inches at the proximal end of the infusion section to about 0.01 inches at the distal end thereof. The largest, i.e., most distal, exit hole 64 is preferably about 0.25 inches from the distal end of the tube 62. In the preferred configuration, the axial separation between adjacent holes 64 is within the range of about 0.125 to 0.25 inches, and more preferably about 3/16 inch. Optionally, the holes 64 may be provided so that adjacent holes are angularly displaced by about 120□ as in the embodiment of FIG. 5. Of course, if too many exit holes 64 are provided, the tube 62 may be undesirably weakened.

Figure 9:
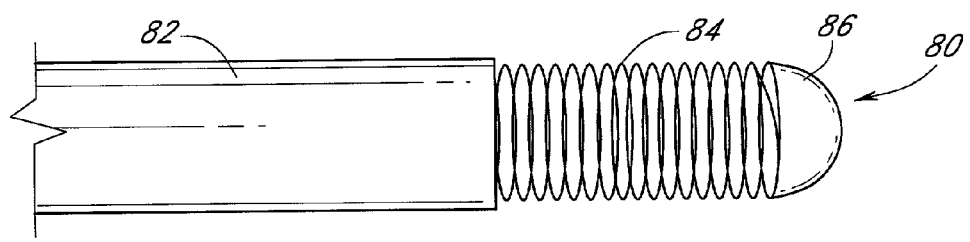
FIG. 9 is a side view of a catheter having features and advantages in accordance with a fifth embodiment of the present invention.
Figure 10A:
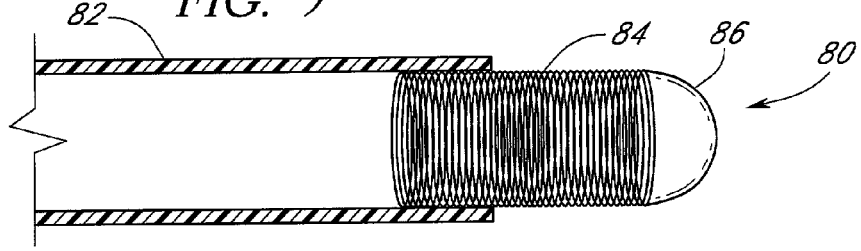
FIG. 10A is a cross-sectional view of the catheter of FIG. 9, illustrating an unstretched state of the spring.
Figure 10B:
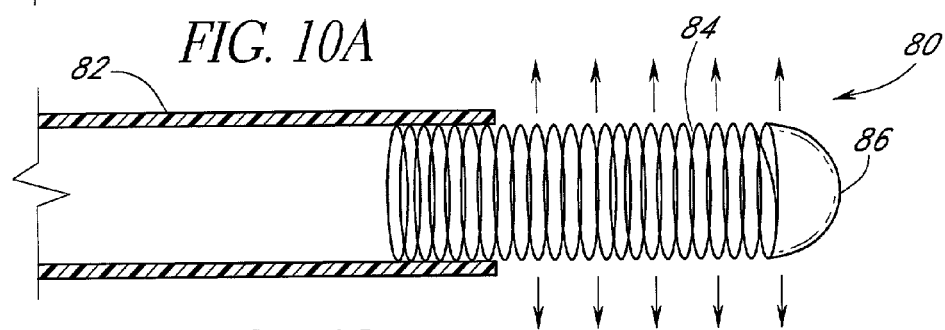
FIG. 10B is a cross-sectional view of the catheter of FIG. 9, illustrating a stretched state of the spring.

FIGS. 9, 10A, and 10B illustrate a catheter 80 according to another embodiment of the present invention. The catheter 80 comprises a tube 82, a "weeping" tubular coil spring 84, and a stop 86. The proximal end of the spring 84 is attached to the distal end of the tube 82 so that the tube and spring each define a portion of a central lumen. A preferably dome-shaped stop 86 is attached to and closes the distal end of the spring 84. The portion of the spring 84 that is distal to the tube 82 comprises the infusion section of the catheter 80. In an unstretched state, shown in FIG. 10A, the spring 84 has adjacent coils in contact with one another so that fluid within the spring and below a threshold dispensation pressure is prevented from exiting the lumen by flowing radially between the coils. The spring 84 has the property of stretching longitudinally, as shown in FIG. 10B, when the fluid pressure is greater than or equal to the threshold dispensation pressure of the spring, thereby permitting the fluid to be dispensed from the lumen by "weeping," i.e., leaking radially outward between the coils. Alternatively, the spring may stretch radially without elongating to permit fluid to weep through the coils of the spring. Further, the spring may stretch both longitudinally and radially to permit weeping, as will be understood by those of skill in the art. Advantageously, the fluid between the coils of the spring is dispensed substantially uniformly throughout the length and circumference of the portion of the spring that is distal to the tube 82, i.e., the infusion section. The catheter 80 can be used for both high or low flow rate fluid delivery.

In use, the catheter 80 is inserted into an anatomical region so that the spring 84 is in a region to which fluid medication is desired to be delivered. The spring is initially in an unstretched state, as shown in FIG. 10A. The fluid is introduced into a proximal end of the tube 82 of the catheter 80 and flows into and through the spring 84 until it reaches the stop 86. As fluid is continually introduced into the proximal end of the tube 82, the fluid builds inside of the spring 84. When the spring 84 is filled with fluid, the fluid pressure rises more quickly. The fluid imparts a force directed radially outward onto the spring coils. As the pressure builds, the outward force becomes larger. Once the fluid pressure rises to the threshold dispensation pressure, the outward force causes the spring coils to separate slightly so that the spring stretches longitudinally, as shown in FIG. 10B. Alternatively, the coils may separate radially, as discussed above. The fluid then flows through the separated coils to be dispensed from the catheter 80. Moreover, the dispensation is advantageously uniform throughout the infusion section of the catheter 80. As fluid is continually introduced into the tube 82, the spring 84 remains stretched to continually dispense fluid to the desired region within the anatomy. If the fluid introduction temporarily ceases, the fluid pressure within the spring 84 may fall below the threshold dispensation pressure. If so, the spring will compress so that the coils are once again adjacent and the fluid is no longer dispensed.

Several spring types will achieve the purposes of this invention. Suitable spring types are 316L or 402L, which can be readily purchased. In a preferred configuration, the spring 84 has about 200 coils per inch along its length. In this configuration, the spring can advantageously sustain a high degree of bending without leaking fluid from within, and only a severe bend will cause adjacent coils to separate. Thus, the spring 84 may be flexed considerably within an anatomical region without causing fluid to leak and therefore be dispensed to only one region within the anatomy. The spring 84 can have any desired length to define the length of the infusion section of the catheter 80. The spring may be formed from a variety of materials, giving due consideration to the goals of strength, flexibility, and safety. A preferred material is stainless steel. In the preferred configuration, the inside and outside diameters of the spring are about 0.02 inches and 0.03 inches, respectively, and the spring wire has a diameter of about 0.005 inches. The proximal end of the spring 84 is preferably concentrically enclosed within the distal end of the tube 82. The spring can be glued to the inside wall of the tube 82 using, for example, a U.V. adhesive, a potting material, or other bonding materials. Alternatively, the spring can be soldered within the tube 82 or be fitted with a proximal plug and tightly plugged into the tube 82.

The tube 82 and stop 86 can be formed from any of a variety of materials, giving due consideration to the goals of flexibility, light-weight, strength, smoothness, and safety. Suitable materials include nylon, polyimide, teflon, and other materials known to those skilled in the art.

Figure 11:
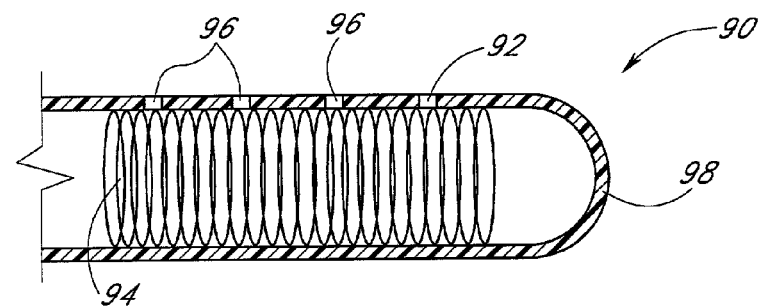
FIG. 11 is a cross-sectional view of a catheter having features and advantages in accordance with a sixth embodiment of the present invention.

FIG. 11 illustrates a catheter 90 according to another embodiment of the present invention. The catheter 90 comprises a distally closed tube 92 and a "weeping" tubular coil spring 94 concentrically enclosed within the tube 92 so that a lumen is defined within the tube and spring. A plurality of exit holes 96 are provided along a length of the tube 92, in the side wall thereof. The length of the tube 92 including such exit holes 96 defines an infusion section of the catheter 90. The exit holes 96 are preferably provided throughout the walls of the infusion section. The infusion section can have any desired length. In the preferred configuration, the axial spacing between adjacent holes 96 is within the range of about 0.125 to 0.25 inches, and more preferably about 3/16 inch. Adjacent holes 96 are preferably angularly spaced apart by about 120°. The spring 94 is preferably enclosed within the infusion section of the catheter and configured similarly to the spring 84 of the embodiment of FIGS. 9, 10A and 10B. The spring 94 is preferably longer than the infusion portion and positioned so that all of the exit holes 96 are adjacent to the spring 94. In this configuration, the fluid is prevented from exiting the lumen without flowing between the spring coils. A stop is preferably attached to the tube to close the distal end thereof. Alternatively, the tube 92 may be formed with a closed distal end. The catheter 90 can be used for high or low flow rate fluid delivery.

In use, the catheter 90 is inserted into an anatomical region so that the infusion section is in a region to which fluid medication is desired to be delivered. The fluid is introduced into a proximal end of the tube 92 of the catheter 90 and flows through the spring 94 until it reaches the closed distal end of the tube 92. As fluid is continually introduced into the proximal end of the tube 92, the fluid builds inside of the spring 94. Eventually, the spring 94 becomes filled with fluid, the fluid pressure rises, and the fluid weeps through the spring coils as described above in connection with the embodiment of FIGS. 9, 10A, and 10B. Moreover, the fluid flows through the spring coils substantially uniformly throughout the length and circumference of the spring 94. The fluid then exits the tube 92 by flowing through the exit holes 96 of the infusion section. The exit holes are preferably equal in size so that the fluid flows at a substantially equal rate through the exit holes, advantageously resulting in a generally uniform distribution of fluid throughout a desired region of the anatomy. As fluid is continually introduced into the catheter 90, the spring 94 remains stretched to continually dispense fluid from the catheter. If the fluid introduction ceases temporarily, the fluid pressure within the spring 94 may fall below the threshold dispensation pressure. If so, the spring may compress so that the coils are once again adjacent and the fluid is no longer dispensed.

In the preferred configuration, the spring 94 and tube 92 are in contact along the entire length of the spring, so that the fluid weeping through the spring is forced to flow through the holes 96 of the infusion section. Preferably, one end of the spring 94 is attached to the inside walls of the tube 92, permitting the other end of the spring to be displaced as the spring stretches. The spring can be glued to the tube 92 with, for example, a U.V. adhesive, potting material, or other bonding materials. Alternatively, an end of the spring can be soldered onto the inner walls of the tube 92. The tube 92 can be formed from any suitable material. The inside walls of the tube 92 are preferably smooth so that the spring can more freely stretch and compress.

Figure 12:
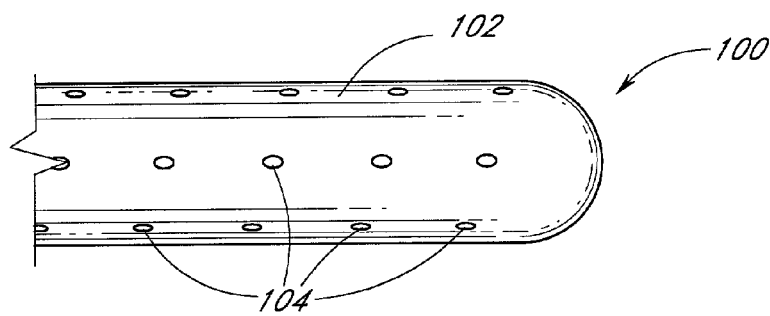
FIG. 12 is a side view of a catheter having features and advantages in accordance with the sixth embodiment of the present invention.

FIG. 12 illustrates a catheter 100 according to another embodiment of the present invention. The catheter 100 comprises a distally closed tube 102 having a plurality of exit holes 104 in side walls of the tube 102. The portion of the tube 102 having exit holes 104 defines an infusion section of the catheter 100. The exit holes 104 are sized to have a combined area of opening that is smaller than the area of any other flow-restricting cross-section or orifice of the catheter. Thus, the exit holes 104 are the flow-restrictor of the catheter 100. In use, the catheter advantageously dispenses fluid through substantially all of the exit holes 104. A fluid introduced into a proximal end of the tube 102 flows through the tube until it reaches the closed distal end thereof. At this point, the fluid builds within the infusion portion of the catheter. The fluid is substantially prevented from flowing through the holes 104, due to their small size. Eventually, the infusion portion of the catheter becomes filled with fluid. As fluid is continually introduced into the proximal end of the tube 102, the fluid pressure begins to build. At some point the pressure becomes sufficiently high to force the fluid through the exit holes 104. Moreover, the fluid flows through substantially all of the exit holes 104.

In this preferred configuration, the exit holes 104 are all equal in size so that the fluid is dispensed at a substantially equal rate through substantially all of the holes. The holes 104 are preferably laser drilled to achieve a very small hole diameter. A preferred diameter of the exit holes 104 is about 0.0002 inches, or about 5 microns. Numerous exit holes 104 may be provided within the tube 102. The holes are advantageously provided throughout the circumference of the infusion portion of the catheter 100, to more uniformly deliver the fluid throughout an anatomical region. A preferred axial spacing between adjacent holes 104 is within the range of about 0.125 to 0.25 inches, and more preferably about 3/16 inch. The catheter 100 can be used for high or low flow rate fluid delivery. The tube 102 can be formed from any of a variety of materials known to those skilled in the art and discussed previously.

Figure 13:
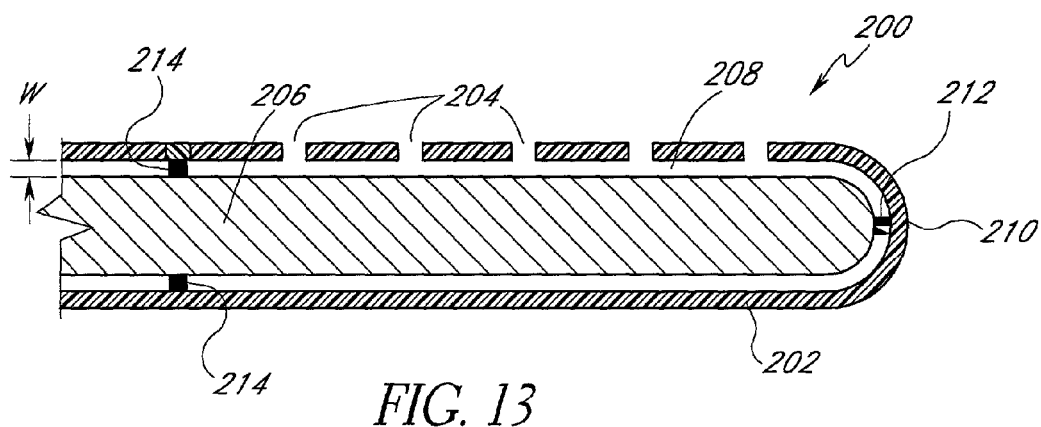
FIG. 13 is a longitudinal cross-sectional view of a catheter having features and advantages in accordance with the seventh embodiment of the present invention.

FIG. 13 illustrates a catheter 200 according to another embodiment of the present invention. Catheter 200 includes a distally closed tube 202 having a plurality of exit holes 204 therein along an infusion section of the catheter, as in the above-described embodiments. The holes 204 are desirably provided throughout the circumference of the tube 202. Enclosed within the tube 202 is an elongated member 206 formed of a porous material. Preferably, the member 206 is generally cylindrical in shape, and solid. Preferably, the member 206 is positioned within the tube 204 so that an annular space 208 is formed between the outer surface of the member 206 and the inner surface of the tube 202. Preferably, the member 206 extends from the distal end 210 of the tube 202 rearwardly to a point proximal of the infusion section of the catheter. Alternatively, the member 206 may extend along only a portion of the infusion section. The member 206 is preferably generally concentric with the tube 202, but non-concentric designs will achieve the advantages of the invention. Preferably, the member 206 is manufactured of a flexible material to assist with the placement of the catheter 200 in the body of a patient.

In operation, fluid medication flowing in the tube 202 saturates the porous member 206 and flows into the annular region 208. Once the member 206 is saturated, the fluid in the member 206 flows into the region 208 and out of the catheter 200 through the exit holes 204. Advantageously, since the fluid pressure is uniform throughout the annular region 208, the fluid flows substantially uniformly through all of the holes 204. There are several advantages of the annular region 208. One advantage is that it tends to optimize the uniformity of flow through the exit holes 204. Also, the member 206 may be formed from a porous material that tends to expand when saturated with liquid. If so, the member 206 preferably expands into the annular region 208 without pressing against the tube 202. This limits the possibility of high pressure regions at the interior surface of the tube 202, which could cause uneven exit flow of the medication within the wound site. Alternatively, the member 206 may expand and come into contact with the tube 202, and still accomplish the goals of the present invention.

The member 206 is formed of a porous material having an average pore size preferably within the range of 0.1–50 microns, and more preferably about 0.45 microns. The radial width W of the annular region 208 is preferably within the range of 0 to about 0.005 microns, and more preferably about 0.003 microns. The member 206 can be formed of any of a variety of materials, giving due consideration to the goals of porosity, flexibility, strength, and durability. A preferred material is Mentek.

Figure 14:
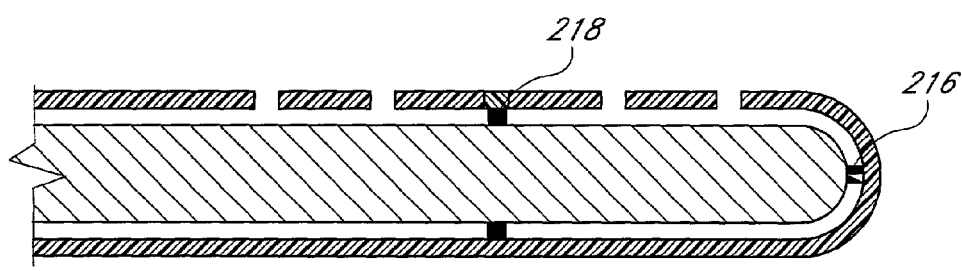
FIGS. 14–16 are longitudinal cross-sectional views of catheters similar to that of FIG. 13, illustrating alternative attachments between the internal porous member and the tube.
Figure 15:
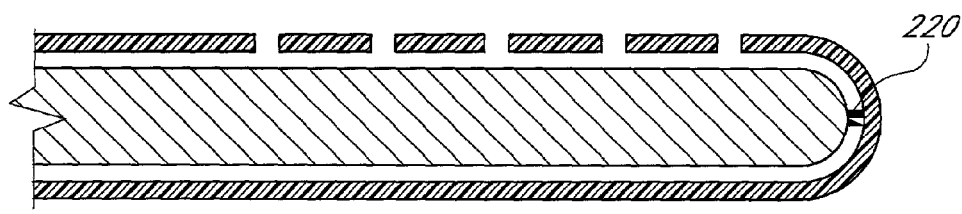
Figure 16:
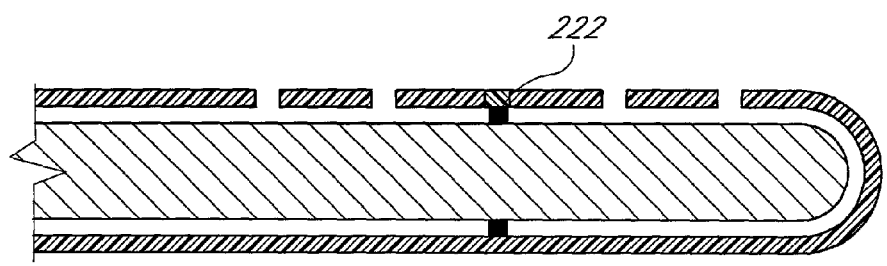

The member 206 can be secured within the tube 202 by the use of an adhesive. In one embodiment, as shown in FIG. 13, the adhesive is applied at the distal end of the member 206 to form a bond with the interior surface of the distal end of the tube 202. Preferably, adhesive is applied at or near the proximal end of the infusion section of the catheter 200. Additionally, the adhesive can be applied to the circumference of the member 206 at any longitudinal position thereof, forming a ring-shaped bond with the interior surface of the tube 202. For example, in the embodiment of FIG. 13, a ring-shaped bond 214 is provided just proximal of the infusion section of the catheter 200. Other configurations are possible. For example, FIG. 14 shows an embodiment in which the adhesive is applied to the distal end of the member 206 to form a bond 216, and also at generally the center of the infusion section to form a ring-shaped bond 218. FIG. 15 shows an embodiment in which the adhesive is applied only to the distal end of the member 206 to form a bond 220. FIG. 16 shows an embodiment in which the adhesive is applied only to the center of the infusion section to form a ring-shaped bond 222. Those of ordinary skill in the art will understand from the teachings herein that the adhesive may be applied in any of a variety of configurations. Thus, for example, adhesive at the distal end of the catheter (i.e., 212, 216, and 220 in FIGS. 13, 14, and 15, respectively) is not required.

In the current best mode of the invention, preferably two bonds are incorporated—one at the most proximal hole and one at the most distal hole of the catheter. Each bond is formed with an adhesive as described below.

The ring-shaped bond 214 can be formed by pouring the adhesive in liquid form through one of the exit holes 204 when the member 206 is in the tube 202. The adhesive, having a generally high viscosity, tends to flow about the circumference of the member 206, rather than into the body of the member. The adhesive thus forms a ring-shaped bond with the tube 202, as will be understood by those of skill in the art. Also, the adhesive plugs the exit hole 204 through which it is poured. Any of a variety of different types of adhesives will be acceptable, a preferred adhesive being Loctite.

Figure 17:
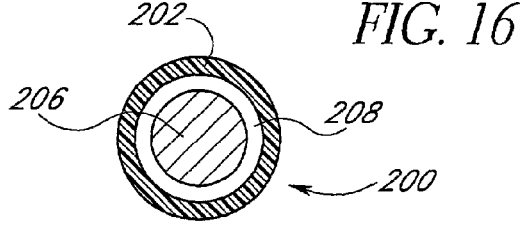
FIG. 17 is a transverse cross-sectional view of a catheter according to FIGS. 13–16, wherein the internal porous member is concentric with the outer tube.
Figure 18:
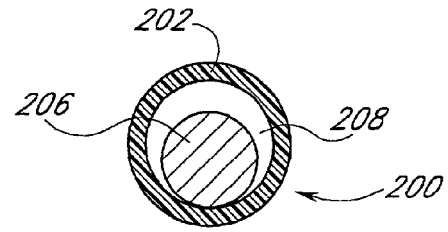
FIG. 18 is a transverse cross-sectional view of a catheter according to FIGS. 13–16, wherein the internal porous member is not concentric with the outer tube.

As mentioned above, the member 206 is preferably concentric with the tube 202. FIG. 17 shows a cross-section of a catheter 200 in which the member 206 is concentrically enclosed within the tube 202. Alternatively, the member 206 may be positioned adjacent to the tube 202, as shown in FIG. 18. The configuration of FIG. 18 may be easier to manufacture than that of FIG. 17, since the member 206 does not have to be centered within the tube 202.

Those of ordinary skill in the art will understand from the teachings herein that the member 206 can be of any desired length and can extend along any desired length of the infusion section of the catheter 200. For example, the member 206 does not have to extend to the distal end of the tube 202. Further, the proximal end of the member 206 may be either distal or proximal to the proximal end of the infusion section.

Figure 19:
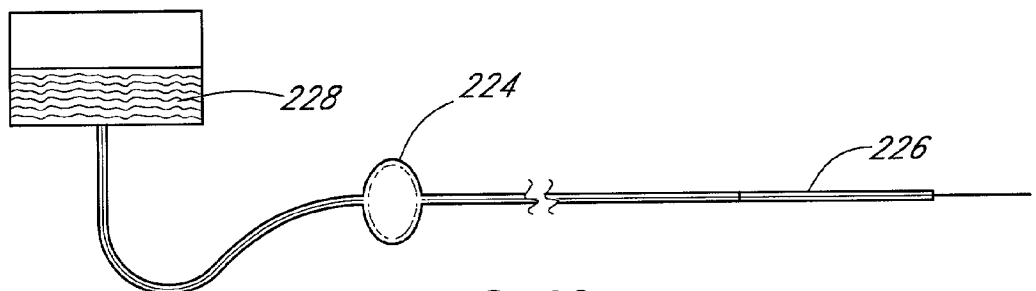
FIG. 19 is a schematic illustration of a catheter of the present invention used in conjunction with an air eliminating filter.

When any of the catheters of the above embodiments is used, the catheter may initially have air inside of the catheter tube. For example, the catheter 200 shown in FIG. 13 may have air inside of the porous material of the member 206. The introduction of liquid medication into the catheter forces the air to flow out of the exit holes. However, this may take several hours. If the catheter is inserted into a patient while air is inside, and liquid medication is introduced into the catheter, the patient's wound site may receive little or no medication until air is expelled from the catheter tube. Thus, it is preferred to run the liquid medication through the catheter prior to inserting the catheter into a patient, to ensure that the air is expelled from the catheter prior to use. Further, with reference to FIG. 19, an air filter 224, as known in the art, can be inserted into the catheter tubing proximal the infusion section 226 of the catheter 200. The filter 224 prevents undesirable air from entering the infusion section 226 of the catheter 200.

Figure 20:
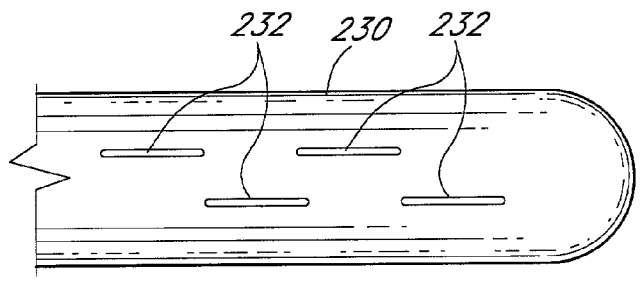
FIG. 20 is a side view of a catheter having features and advantages in accordance with the eighth embodiment of the present invention.
Figure 21:
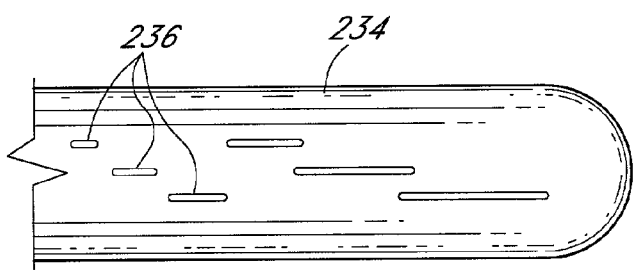
FIG. 21 is a side view of a catheter having features and advantages in accordance with the ninth embodiment of the present invention.

FIGS. 20 and 21 illustrate catheter tubes having elongated exit holes or slots. These catheter tubes may be used in place of the catheter tubes shown and described above. FIG. 20 shows a tube 230 having exit holes or slots 232 that are elongated in the longitudinal direction of the tube 230. The slots 232 are preferably provided throughout the circumference of the tube 230, along the infusion section of the catheter. Compared to smaller exit holes, the elongated slots 232 tend to increase the flowrate of fluid exiting the catheter, by reducing the flow impedance experienced by the fluid. Preferably, the slots 232 may be oriented longitudinally on the catheter body so as not to compromise the structural integrity of the catheter 200, as will be easily understood by those of skill in the art.

FIG. 21 shows a tube 234 having exit holes or slots 236 whose lengths increase along the length of the tube in the distal direction. In the illustrated embodiment, the slots nearer to the proximal end of the infusion section of the tube 234 are shorter in length than the slots nearer to the distal end of the infusion section. As in the embodiment of FIG. 8, the catheter tube 234 advantageously provides substantially uniform fluid delivery through substantially all of the exit slots 236, under relatively high flow rate conditions. This is because the larger size of the more distal slots compensates for their increased flow resistance and pressure drop. In other words, since the more distal slots are larger than the more proximal slots, there is a greater flow rate through the more distal slots than there would be if they were the same size as the more proximal slots. Advantageously, the slots 236 are provided in a gradually increasing length, which results in substantially uniform fluid delivery. Further, the elongated slots result in generally higher exit flowrates, as in the embodiment of FIG. 20.

With regard to all of the above embodiments of catheters, an independent guide wire lumen may be provided within or adjacent to the lumen(s) disclosed, as will be understood by those skilled in the art.

Figure 22:
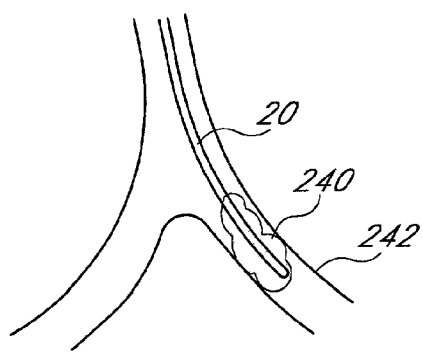
FIG. 22 is a schematic illustration of the use of a catheter of the present invention for treating a blood clot.

The catheters of the present invention can be used in various medical applications. With reference to FIG. 22, in one exemplary application a catheter 20 (reference numeral 20 is used to identify the catheter, but any of the above-described catheters can be used) is inserted into a blood clot 240 inside of a vein or artery 242. Preferably, the infusion section of the catheter is within the blood clot 240. Liquid medication is preferably introduced into the proximal end of the catheter tube. Advantageously, the medication exits the catheter 20 at a uniform rate throughout the infusion section to dissolve the clot 240.

As will be easily understood by those of skill in the art, any of the catheter embodiments described herein may be used in a variety of applications including, but not limited to, peripheral nerve blocks, intrathecal infusions, epideral infusions, intravascular infusions, intraarterial infusions and intraarticular infusions, as well as in wound site pain management.

In addition, any of the catheters disclosed herein may be integral with a fluid line eminating from an infusion pump as opposed to being an independent catheter designed to be connected or secured to an infusion pump.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A catheter for the delivery of a fluid to an anatomical region, comprising:
    an elongated, tubular catheter body having a closed distal end, a distal portion of said catheter body defining an infusion section of said catheter, said infusion section configured to permit fluid to pass through said catheter body;
    a member having adjacent coils, wherein an outer surface of said adjacent coils, in a relaxed position of said member, are in contact with one another in at least a portion of said member, said member having a first end and a second end and being enclosed within a lumen of said catheter body and extending at least a length of said infusion section; and
    wherein at least one of said first end and said second end of said member is secured to said catheter body.

2. The catheter of claim 1, wherein only one of said first end and said second end of said member is secured to said catheter body.

3. The catheter of claim 1, wherein said infusion section of said catheter comprises a plurality of exit holes in said catheter body.

4. The catheter of claim 1, wherein said member has about 200 coils per inch of length.

5. The catheter of claim 1, wherein a portion of an outer surface of said member contacts a portion of an inner surface of said catheter body.

6. The catheter of claim 1, wherein said member is secured to said catheter body with a U.V. adhesive.

7. A catheter for the uniform delivery of fluid throughout an anatomical region, comprising:
    an elongated tube having a closed distal end and a plurality of exit holes in a side wall of said tube, said exit holes provided along a length of said tube defining an infusion section of said catheter, said tube being sized to be inserted into an anatomical region; and
    a member having adjacent coils, wherein an outer surface of said adjacent coils, in a relaxed position of said member, are in contact with one another in at least a portion of said member, said member having a first end and a second end and being enclosed within a lumen of said tube and extending at least a length of said infusion section, one of said first end and said second end being secured to said tube;
    wherein said catheter is configured so that a fluid introduced into a proximal end of said tube will flow between said coils of said member and through said exit holes.

8. The catheter of claim 7, wherein said member has about 200 coils per inch of length.

9. The catheter of claim 7, wherein a portion of an outer surface of said member contacts a portion of an inner surface of said side wall of said tube.

10. The catheter of claim 7, wherein said member is secured to said tube with a U.V. adhesive.

11. A catheter for the delivery of a fluid to an anatomical region, comprising:
    an elongated, tubular catheter body having a closed distal end, a distal portion of said catheter body defining an infusion section of said catheter, said infusion section configured to permit fluid to pass through said catheter body;
    a member comprising a plurality of coils adjacent to one another, wherein in a relaxed position of said member an outer surface of each of said coils contacting at least a portion of an outer surface of an adjacent one of said coils, said member having a first end and a second end and being enclosed within a lumen of said catheter body and extending at least a length of said infusion section; and wherein at least one of said first end and said second end of said member is secured to said catheter body.

12. The catheter of claim 11, wherein only one of said first end and said second end of said member is secured to said catheter body.

13. The catheter of claim 11, wherein said infusion section of said catheter comprises a plurality of exit holes in said catheter body.

14. The catheter of claim 11, wherein said member has about 200 coils per inch of length.

15. The catheter of claim 11, wherein a portion of an outer surface of said member contacts a portion of an inner surface of said catheter body.

16. The catheter of claim 11, wherein said member is secured to said catheter body with a U.V. adhesive.

17. The catheter of claim 1, wherein said adjacent coils in a section of said member between said first and second ends are not secured to said catheter body.

18. The catheter of claim 1, wherein said member is stainless steel.

19. The catheter of claim 7, wherein said adjacent coils in a section of said member between said first and second ends are not secured to said catheter body.

20. The catheter of claim 7, wherein said member is stainless steel.

21. The catheter of claim 11, wherein said coils in a section of said member between said first and second ends are not secured to said catheter body.

22. The catheter of claim 11, wherein said member is stainless steel.

23. A catheter, comprising:
an elongated, tubular catheter body having a closed distal end, a distal portion of said catheter body defining an fluid passing section of said catheter, said fluid passing section configured to permit fluid to pass through said catheter body;
a member comprising a plurality of coils adjacent to one another, an outer surface of each of said coils contacting at least a portion of an outer surface of an adjacent one of said coils, said member having a first end and a second end and being enclosed within a lumen of said catheter body and extending at least a length of said fluid passing section; and
wherein at least a portion of said member is secured to said catheter body.

24. The catheter of claim 23, wherein only one of said first end and said second end of said member is secured to said catheter body.

25. The catheter of claim 23, wherein said fluid passing section of said catheter comprises a plurality of exit holes in said catheter body.

26. The catheter of claim 23, wherein said member has about 200 coils per inch of length.

27. The catheter of claim 23, wherein a portion of an outer surface of said member contacts a portion of an inner surface of said catheter body.

28. The catheter of claim 23, wherein said member is secured to said catheter body with a U.V. adhesive.

29. The catheter of claim 23, wherein said coils in a section of said member between said first and second ends are not secured to said catheter body.

30. The catheter of claim 23, wherein said member is stainless steel.

* * * * *